United States Patent
Schmidt et al.

(10) Patent No.: US 11,931,386 B2
(45) Date of Patent: Mar. 19, 2024

(54) COMPOSITIONS AND METHODS FOR INCREASING BUTYRATE PRODUCTION

(71) Applicant: THE REGENTS OF THE UNIVERSITY OF MICHIGAN, Ann Arbor, MI (US)

(72) Inventors: Thomas M. Schmidt, Ann Arbor, MI (US); Nielson Baxter, Ann Arbor, MI (US); Kwi Kim, Ann Arbor, MI (US); Alexander Schmidt, Ann Arbor, MI (US); Arvind Venkataraman, Ann Arbor, MI (US); Clive Waldron, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 72 days.

(21) Appl. No.: 16/642,557

(22) PCT Filed: Aug. 29, 2018

(86) PCT No.: PCT/US2018/048454
§ 371 (c)(1),
(2) Date: Feb. 27, 2020

(87) PCT Pub. No.: WO2019/046372
PCT Pub. Date: Mar. 7, 2019

(65) Prior Publication Data
US 2021/0077546 A1    Mar. 18, 2021

Related U.S. Application Data

(60) Provisional application No. 62/552,848, filed on Aug. 31, 2017.

(51) Int. Cl.
| | |
|---|---|
| A61K 35/745 | (2015.01) |
| A61K 9/00 | (2006.01) |
| A61K 9/48 | (2006.01) |
| A61K 31/718 | (2006.01) |
| A61K 35/742 | (2015.01) |
| A61P 1/00 | (2006.01) |

(52) U.S. Cl.
CPC .......... *A61K 35/745* (2013.01); *A61K 9/0031* (2013.01); *A61K 9/0053* (2013.01); *A61K 9/48* (2013.01); *A61K 31/718* (2013.01); *A61K 35/742* (2013.01); *A61P 1/00* (2018.01)

(58) Field of Classification Search
CPC .......................... A61K 35/745; A61K 31/718
See application file for complete search history.

(56) References Cited

U.S. PATENT DOCUMENTS

| | | | | |
|---|---|---|---|---|
| 2007/0207132 A1* | 9/2007 | Speelmans | ............. | A61K 35/74 424/93.45 |
| 2016/0143961 A1* | 5/2016 | Berry | .................... | A61K 35/741 |
| 2016/0143962 A1* | 5/2016 | Berry | .................... | A61K 35/742 |
| 2016/0213702 A1* | 7/2016 | Von Maltzahn | ...... | A61K 31/715 |
| 2016/0271189 A1* | 9/2016 | Cutcliffe | ................ | A61K 35/74 |

OTHER PUBLICATIONS

Nucleotide BLAST: Align two or more sequences using BLAST, alignment run date: Feb. 22, 2022 (Year: 2022).*
Melissa A. E. Lawson et al., Breast milk-derived human milk oligosaccharides promote Bifidobacterium interactions within a single ecosystem, The ISME Journal (2020) 14:635-648 (Year: 2020).*
Rocio Martin et al., Isolation of Bifidobacteria from Breast Milk and Assessment of the Bifidobacterial Population by PCR-Denaturing Gradient Gel Electrophoresis and Quantitative Real-Time PCR, Applied and Environmental Microbiology, Feb. 2009, p. 965-969 (Year: 2009).*
Juan M. Rodriguez, The Origin of Human Milk Bacteria: Is There a Bacterial Entero-Mammary Pathway during Late Pregnancy and Lactation?, American Society for Nutrition. Adv. Nutr. 5: 779-784, 2014 (Year: 2014).*
Ava K. Kiser et al., Management of Diseases Without Current Treatment Options Something Can Be Done, JAMA. Apr. 22, 2009; 301 (16): 1708-1709 (Year: 2009).*
Thomas Wnorowski, Comprehensive Guide to Butyrate: What it is, Benefits, Side Effects, & More, publication date: Jun. 10, 2020 (Year: 2020).*
Cleveland Clinic (Cleveland Clinic, Crohn's Disease: Symptoms, Causes, Management & Treatment, downloaded in Oct. 7, 2022 (Year: 2022).*
Xiaolei Ze et al., Ruminococcus bromii is a keystone species for the degradation of resistant starch in the human colon, The ISME Journal (2012) 6, 1535-1543 (Year: 2012).*
Kai Nie et al., *Roseburia intestinalis*: A Beneficial Gut Organism From the Discoveries in Genus and Species, Frontiers in Cellular and Infection Microbiology, vol. 11, Article 757718, publication date: Nov. 22, 2021 (Year: 2021).*
Jung-Hye Choi et al., *Bifidobacterium faecale* sp. nov., isolated from human faeces, International Journal of Systematic and Evolutionary Microbiology (2014), 64, 3134-3139) (Year: 2014).*
International Search Report and Written Opinion for PCT/US18/48454, dated Dec. 13, 2018. 16 pages.
Abt et al., Commensal bacteria mediated defenses against pathogens. Curr Opin Immunol. Aug. 2014;29:16-22.
Abt et al., The dynamic influence of commensal bacteria on the immune response to pathogens. Curr Opin Microbiol. Feb. 2013;16(1):4-9.

(Continued)

*Primary Examiner* — Mark V Stevens
*Assistant Examiner* — Alparslan Asan
(74) *Attorney, Agent, or Firm* — Casimir Jones, S.C.; Tanya A. Arenson

(57) ABSTRACT

Provided herein are compositions and methods for increasing butyrate production in a subject. In particular, provided herein are compositions, probiotic compositions, and combinations thereof that promote butyrate production in a subject.

14 Claims, 8 Drawing Sheets
Specification includes a Sequence Listing.

(56) References Cited

OTHER PUBLICATIONS

Allen-Vercoe et al., *Anaerostipes hadrus* comb. nov., a dominant species within the human colonic microbiota; reclassification of Eubacterium hadrum Moore et al. 1976. Anaerobe. Oct. 2012;18(5):523-9.
Andoh et al., Physiological and anti-inflammatory roles of dietary fiber and butyrate in intestinal functions. JPEN J Parenter Enteral Nutr. Sep.-Oct. 1999;23(5 Suppl):S70-3.
Archer et al., Butyrate inhibits colon carcinoma cell growth through two distinct pathways. Surgery. Aug. 1998;124(2):248-53.
Birt et al., Resistant starch: promise for improving human health. Adv Nutr. Nov. 6, 2013;4(6):587-601.
Bourassa et al., Butyrate, neuroepigenetics and the gut microbiome: Can a high fiber diet improve brain health? Neurosci Lett. Jun. 20, 2016;625:56-63.
Duncan et al., Lactate-utilizing bacteria, isolated from human feces, that produce butyrate as a major fermentation product. Appl Environ Microbiol. Oct. 2004;70(10):5810-7.
Furusawa et al., Commensal microbe-derived butyrate induces the differentiation of colonic regulatory T cells. Nature. Dec. 19, 2013;504(7480):446-50.
Gao et al., Butyrate Improves Insulin Sensitivity and Increases Energy Expenditure in Mice. Diabetes 2009, 58(7):1509-1517.
Hamer et al., Review article: the role of butyrate on colonic function. Aliment Pharmacol Ther. Jan. 15, 2008;27(2):104-19.
Hassig et al., Fiber-derived butyrate and the prevention of colon cancer. Chem Biol. Nov. 1997;4(11):783-9.
Kamada et al., Control of pathogens and pathobionts by the gut microbiota. Nat Immunol. Jul. 2013;14(7):685-90.
Kamada et al., Role of the gut microbiota in immunity and inflammatory disease. Nat Rev Immunol. May 2013;13(5):321-35.
Lattimer et al., Effects of dietary fiber and its components on metabolic health. Nutrients. Dec. 2010;2(12):1266-89.
Lazarova et al., Butyrate induced changes in Wnt-signaling specific gene expression in colorectal cancer cells. BMC Res Notes. Apr. 9, 2014;7:226.
Leitch et al., Selective colonization of insoluble substrates by human faecal bacteria. Environ Microbiol. Mar. 2007;9(3):667-79.
Lin et al., Butyrate and propionate protect against diet-induced obesity and regulate gut hormones via free fatty acid receptor 3-independent mechanisms. PLoS One. 2012;7(4):e35240. 9 pages.
Marteau. Butyrate-producing bacteria as pharmabiotics for inflammatory bowel disease. Gut. Dec. 2013;62(12):1673.
Mathewson et al., Gut microbiome-derived metabolites modulate intestinal epithelial cell damage and mitigate graft-versus-host disease. Nat Immunol. May 2016;17(5):505-513.
Mikkelsen et al., Effect of Antibiotics on Gut Microbiota, Gut Hormones and Glucose Metabolism. PLoS One. Nov. 12, 2015;10(11):e0142352. 14 pages.
Moens et al., Inulin-type fructan degradation capacity of Clostridium cluster IV and XIVa butyrate-producing colon bacteria and their associated metabolic outcomes. Benef Microbes. May 30, 2017;8(3):473-490.
Peng et al., Butyrate Enhances the Intestinal Barrier by Facilitating Tight Junction Assembly via Activation of AMP-Activated Protein Kinase in Caco-2 Cell Monolayers. J Nutr. Sep. 2009;139(9):1619-25.
Ruemmele et al., Butyrate induced Caco-2 cell apoptosis is mediated via the mitochondrial pathway. Gut. Jan. 2003;52(1):94-100.
Scardovi V, Trovatelli LD: The fructose-6-phosphate shunt as a peculiar pattern of hexose degradation in the genus *Bifidobacterium*. Annals of Microbiology 1965, 15:19-29.
Segain et al., Butyrate inhibits inflammatory responses through NFkappaB inhibition: implications for Crohn's disease. Gut. Sep. 2000;47(3):397-403.
Slavin. Fiber and prebiotics: mechanisms and health benefits. Nutrients. Apr. 22, 2013;5(4):1417-35.
Slavin. Position of the American Dietetic Association: health implications of dietary fiber. J Am Diet Assoc. Oct. 2008;108(10):1716-31.
Tremaroli et al., Functional interactions between the gut microbiota and host metabolism. Nature. Sep. 13, 2012;489(7415):242-9.
Velazquez et al., Butyrate. Potential role in colon cancer prevention and treatment. Adv Exp Med Biol. 1997;427:169-81.
Wang et al., Sodium butyrate induces human colon carcinoma HT-29 cell apoptosis through a mitochondrial pathway. J Int Med Res. May-Jun. 2009;37(3):803-11.
Yadav et al., Beneficial metabolic effects of a probiotic via butyrate-induced GLP-1 hormone secretion. J Biol Chem. Aug. 30, 2013;288(35):25088-25097.
Ze et al., Ruminococcus bromii is a keystone species for the degradation of resistant starch in the human colon. ISME J 2012, 6(8):1535-1543.
Vidrine, K et al., Resistant starch from high amylose maize (HAM-RS2) and dietary butyrate reduced abdominal fat by a different apparent mechanism. Obesity (Silver Spring), Feb. 2014;22(2) : 344-8.†
Nielsen, Tina S et al., Diets high in resistant starch and arabinoxylan modulate digestion processes and SCFA pool size in the large intestine and faecal microbial compstion in pigs. Br J Nutr. Dec. 14, 2014;112(11) :1837-49.†
Brown, I et al., Fecal numbers of bifidobacteria are higher in pigs fed Bifidobacterium longum with a high amylose cornstarch than with a low amylose cornstarch. J Nutr. Sep. 1997;127(9) :1822-7.†

\* cited by examiner
† cited by third party

COMPOSITIONS AND METHODS FOR INCREASING BUTYRATE PRODUCTION

This application is a 371 U.S. National Phase Entry of pending International Application No. PCT/US2018/048454, filed Aug. 29, 2018, which claims the benefit of U.S. Provisional Application No. 62/552,848, filed Aug. 31, 2017, which are incorporated herein by reference in their entireties.

FIELD OF THE DISCLOSURE

Provided herein are compositions and methods for increasing butyrate production in a subject. In particular, provided herein are compositions, probiotic compositions, and combinations thereof that promote butyrate production in a subject.

BACKGROUND

Short-chain fatty acids (SCFAs) are predominant end products of bacterial fermentation in the human colon and are known to have wide-ranging impacts on host physiology. Butyrate in particular is important for maintaining health via regulation of the immune system (Furusawa Y, et al., *Nature* 2013, 504(7480):446-450), maintenance of the epithelial barrier (Peng L, et al., *J Nutr* 2009, 139(9):1619-1625; Ruemmele F M, et al., *Gut* 2003, 52(1):94-100), and promoting satiety following a meal (Mikkelsen K H, et al., *PLoS One* 2015, 10(11):e0142352). It may be protective against several diseases, including colorectal cancer (Wang L, et al., *J Int Med Res* 2009, 37(3):803-811), inflammatory bowel disease (Segain J P, et al., *Gut* 2000, 47(3):397-403), graft-versus-host disease (Mathewson N D, et al., *Nat Immunol* 2016, 17(5):505-513), diabetes (Gao Z, et al., *Diabetes* 2009, 58(7):1509-1517), and obesity (Gao et al., supra; Lin H V, et al., *PLoS One* 2012, 7(4):e35240). Therefore, stimulating butyrate production by the gut microbiome is useful for sustaining health and treating and preventing diseases.

Compositions and methods for promoting butyrate production are needed.

SUMMARY OF THE DISCLOSURE

Provided herein are compositions and methods for increasing butyrate production in a subject. In particular, provided herein are compositions, probiotic compositions, and combinations thereof that promote butyrate production in a subject.

Provided herein is a method of increasing butyrate levels in the intestine of a subject, comprising: administering a carbohydrate source and at least one first bacteria selected from, for example, bacteria belonging to the taxons identified as *Bifidobacterium* spp., *Clostridium* seq 176, sequence 100, or *Ruminococcus bromii*. In some embodiments, the *Bifidobacterium* spp. is *Bifidobacterium faecale*. In some embodiments, the method further comprises the step of administering a second bacteria selected from, for example, bacteria belonging to the taxons identified as *Faecalibacterium prausnitzii, Eubacterium rectale, Roseburia* spp., *Eubacterium halii*, or *Anaerostipes hadrus*. In some embodiments, the *Roseburia* spp. is *Roseburia faecis, Roseburia intestinalis*, or *Roseburia inulinivorans*. In some embodiments, *Clostridium* seq 176 comprises bacteria with a 16S V4 region sequence of SEQ ID NO:1 or bacteria with a 16S V4 region sequences at least 95% identical or homologous to SEQ ID NO:1 (e.g., at least 95%, 96%, 97%, 98%, 99%, 99.5%, or 99.9% identical or homologous to SEQ ID NO:1). In some embodiments, sequence 100 comprises bacteria with a 16S V4 region sequence of SEQ ID NO:2 or bacteria with a 16S V4 region sequences at least 95% identical or homologous to SEQ ID NO:2 (e.g., at least 95%, 96%, 97%, 98%, 99%, 99.5%, or 99.9% identical or homologous to SEQ ID NO:2). In some embodiments, the first or second bacteria is one or more of *Eubacterium rectale* (ATCC 33656), *Faecalibacterium prausnitzii* (ATCC 27768), *Bifidobacterium longum* (ATCC 35183), *Eubacterium hallii* (ATCC 27751), *Ruminococcus bromii* (ATCC 27255), *Bifidobacterium adolescentis* (ATCC 15703), *Bifidobacterium bifidum* (ATCC 29521), *Bifidobacterium breve* (ATCC 15700), *Bifidobacterium pseudolongum* (ATCC 25526), *Bifidobacterium catenulatum* (ATCC 27539), or *Bifidobacterium angulatum* (ATCC 27670).

In some embodiments, the carbodyrate source is a resistant starch (e.g., corn, a corn product (e.g. corn starch), potato, green banana starch, a potato product (e.g., potato starch), or inulin). In some embodiments, the first and/or second bacteria are encapsulated for oral administration and release in the intestine. In some embodiments, the carbohydrate source and the first and/or second bacteria are administered in the same or different compositions. In some embodiments, the carbohydrate and the first and second bacteria are administered orally or rectally (e.g., in a suppository). In some embodiments, the subject is a human. In some embodiments, the butyrate is increased relative to a control (e.g., the level in an individual not administered the carbohydrate and the first and second bacteria, the level in an individual diagnosed with a disease or conditions related to low butyrate levels, or an sub-optimal level of butyrate). In some embodiments, the increased levels of butyrate result in a decrease in signs or symptoms of a disease or condition associated with low levels of butyrate. In some embodiments, the disease or condition is, for example, type II diabetes, metabolic syndrome, obesity, cancer (e.g., colorectal cancer), neurological disorders, or graft versus host disease (e.g. associated with bone marrow transplant).

Certain embodiments provide a method of increasing butyrate levels in the intestine of a subject, comprising: administering a carbohydrate source and at least one second bacteria selected from, for example, bacteria belonging to the taxons identified as *Faecalibacterium prausnitzii, Eubacterium rectale, Roseburia* spp., *Eubacterium halii*, or *Anaerostipes hadrus* and optionally a first bacteria selected from, for example, bacteria belonging to the taxons identified as *Bifidobacterium* spp., *Clostridium* seq 176, sequence 100, or *Ruminococcus bromii*.

Further embodiments provide a method of treating or preventing a disease or condition associated with low levels of butyrate, comprising: administering a carbohydrate source and at least one first bacteria selected from, for example, bacteria belonging to the taxons identified as *Bifidobacterium* spp., *Clostridium* seq 176, sequence 100, or *Ruminococcus bromii*.

Additional embodiments provide the use of a carbohydrate source and at least one first bacteria selected from, for example, bacteria belonging to the taxons identified as *Bifidobacterium* spp., *Clostridium* seq 176, sequence 100, or *Ruminococcus bromii* to increase butyrate levels in the intestine of a subject or to treat or prevent a disease or condition associated with low levels of butyrate.

Yet other embodiments provide a composition, comprising: a carbohydrate source and at least one first bacteria selected from, for example bacteria belonging to the taxons identified as, *Bifidobacterium* spp., *Clostridium* seq 176, sequence 100, or *Ruminococcus bromii*.

Still further embodiments provide a kit, comprising: a) a first container comprising a carbohydrate source; and/or b) a second container comprising at least one first bacteria selected from, for example, bacteria belonging to the taxons identified as *Bifidobacterium* spp., *Clostridium* seq 176, sequence 100, or *Ruminococcus bromii*.

Certain embodiments provide methods of determining a treatment, comprising: a) assaying a sample (e.g., a fecal sample) from a subject for the presence of at least one bacteria selected from, for example, bacteria belonging to the taxons identified as *Bifidobacterium* spp., *Clostridium* seq 176, sequence 100, or *Ruminococcus bromii*; and b) determining a treatment based on the presence of the bacteria. In some embodiments, the treatment comprises administering a composition comprising a resistant starch to the subject when the bacteria are present and a composition comprising at least one bacteria selected from, for example, bacteria belonging to the taxons identified as *Bifidobacterium* spp., *Clostridium* seq 176, sequence 100, and *Ruminococcus bromii* and a resistant starch when the bacteria are not present in the sample.

Additional embodiments are provided herein.

DEFINITIONS

Figure 1:
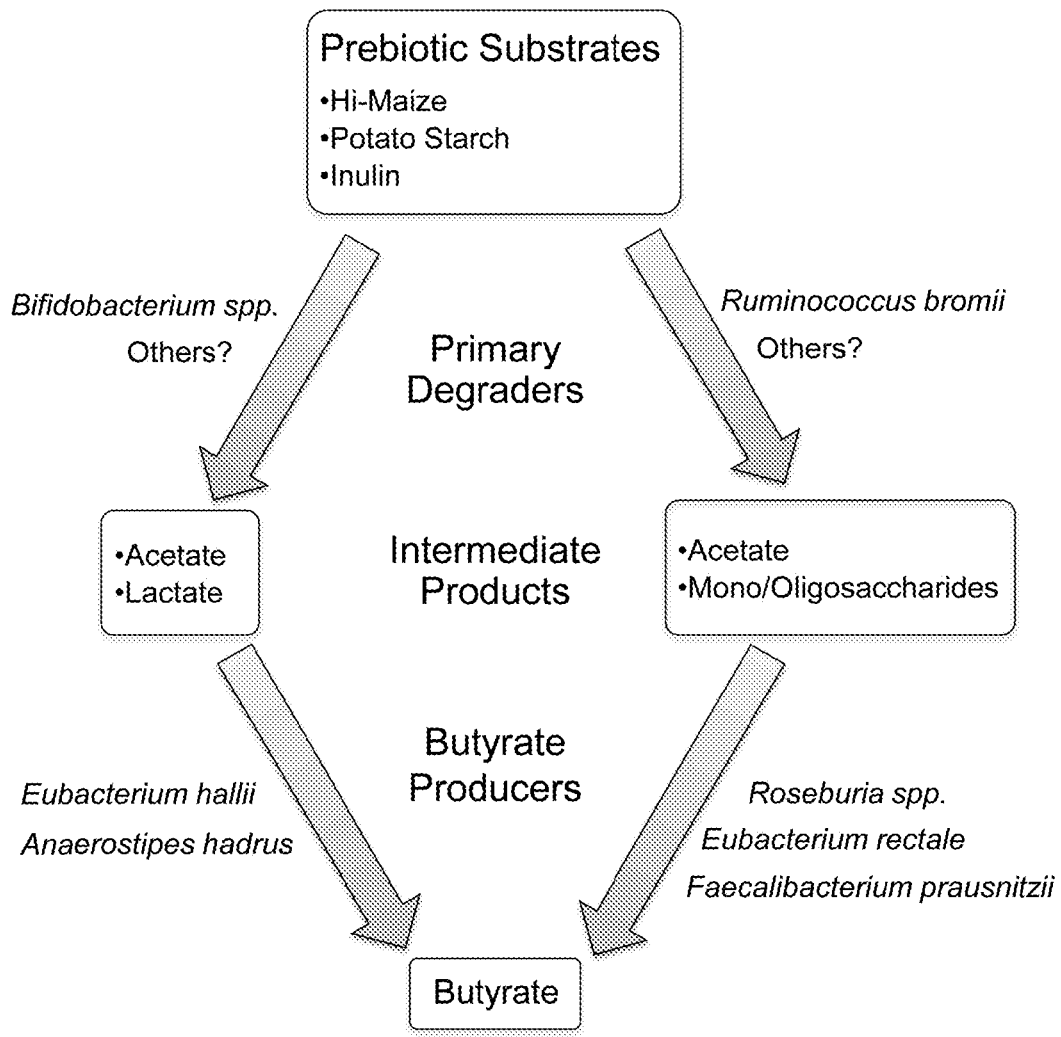
FIG. 1 shows a model for two alternative pathways for stimulating butyrate production with dietary fibers.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present disclosure.

A "subject" is an animal such as vertebrate, preferably a domestic animal or a mammal. Mammals are understood to include, but are not limited to, murines, simians, humans, bovines, cervids, equines, porcines, canines, felines etc.

An "effective amount" is an amount sufficient to effect beneficial or desired results. An effective amount can be administered in one or more administrations.

"Co-administration" refers to administration of more than one agent or therapy to a subject. Co-administration may be concurrent or, alternatively, the agents or materials described herein may be administered in advance of or following the administration of the other agent(s) or materials. One skilled in the art can readily determine the appropriate dosage for co-administration.

"Administration" refers to the delivery of one or more agents or therapies to a subject. The present disclosure is not limited to a particular mode of administration. In some embodiments, compositions described herein are delivered orally. In some embodiments, compositions are delivered rectally or through another suitable delivery method.

As used herein, the term "toxic" refers to any detrimental or harmful effects on a cell or tissue.

A "pharmaceutical composition" is intended to include the combination of an active agent with a carrier, inert or active, making the composition suitable for diagnostic or therapeutic use in vivo, in vitro, or ex vivo.

As used herein, the term "pharmaceutically acceptable carrier" encompasses any of the standard pharmaceutical carriers, such as a phosphate buffered saline solution, water, and an emulsion, such as an oil/water or water/oil emulsion, and various types of wetting agents. The compositions also can include stabilizers and preservatives. For examples of carriers, stabilizers and adjuvants see Martin, Remington's Pharmaceutical Sciences, 15th Ed., Mack Publ. Co., Easton, Pa. (1975).

As used herein, the term "nutraceutical," refers to a food substance or part of a food, which includes a bacterium as described herein. Nutraceuticals can provide medical or health benefits, including the prevention, treatment, or cure of a disorder.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the terms "resistant starch" and "RS" refer to any starch that is not digested in the small intestine but passes to the large bowel. "Resistant starch" includes naturally occurring resistant starches and non-resistant starches that are made resistant through a manufacturing process (e.g., by encapsulation, or by chemical modification or other means). The term includes starches that are partially resistant but processed to increase the RS fraction, and processes that produce RS unintentionally (e.g., not engineered specifically to product RS). In some embodiments, RS pass through the intestines completely undigested. In some embodiments, RS are digested very slowly or incompletely.

In some embodiments, RS starches are classified into 5 subtypes, RS1-5 (See e.g., Raigond et al., Journal of the Science of Food and Agriculture, 95:1968 (2015); herein incorporated by reference in its entirety). In some embodiments RS1 comprises starches that are physically inaccessible to digestion (e.g., whole grains or seeds with intact cell walls). In some embodiments, RS2 comprises native starch granules that are protected from digestion by conformation or structure (e.g., raw potatoes or green bananas). In some embodiments, RS3 comprises physical modified starches (e.g., retrograded amylase or other starch such as cooked and cooled potatoes). In some embodiments, RS4 comprises starches that have been chemically modified (e.g., etherized, esterified or cross-bonded with chemicals) to decrease their digestibility. In some embodiments, RS5 comprises RS arising from the formation of amylose-lipid complexes during food process or under controlled conditions.

Examples or RS suitable for use in embodiments of the present disclosure include, but are not limited to, green banana starch, corn starch, potato starch, rice starch, cassava starch, tapioca starch, plantain starch, inulin, or whole or processed foods comprising such RS.

As used herein, the term "disease or conditions related to low butyrate levels" refers to any disease or condition associated with low or reduced levels of butyrate (e.g., in the intestine). In some embodiments, the disease or condition includes, but is not limited to, type II diabetes, metabolic syndrome, obesity, neurological disorders (See e.g., Bourassa et al., *Neuroscience Letters* 625 (2016) 56-63; herein incorporated by reference in its entirety), cancer (e.g., colorectal cancer), or graft versus host disease.

As used herein, the term "sub-optimal level of butyrate" refers to a level of butyrate (e.g. in the intestine) demonstrated to be associated with a disease or condition.

As used herein, the terms "probiotic" and "probiotic compositions" are used interchangeable to refer to live microorganisms (e.g., bacteria) that provide health benefits when consumed or otherwise administered (e.g., orally or rectally).

As used herein, the term "carbohydrate" refers to a biological molecule comprising carbon (C), hydrogen (H) and oxygen (O) atoms, usually with a hydrogen-oxygen atom ratio of 2:1 (e.g., with the empirical formula $C_m(H2O)n$, m can be different from n. Carbohydrates may be simple (e.g., mono or disaccharides) or complex (e.g., comprising longer straight or branched saccharides). Examples include, but are not limited to, starches, sugars, and the like.

As used herein, the term "taxon" refers to a group of one or more populations of an organism or organisms that form a unit. A taxon is usually known by a particular name and given a particular ranking, especially if and when it is accepted or becomes established. In some embodiments, taxons are defined by NCBI taxonomy systems. In some embodiments, taxons are defined by the sequence of a marker gene (e.g., V4 region of the 16S ribosomal RNA sequence). For example, in some embodiments, bacteria with V4 sequences that are at least 95% identical to the sequences described herein (e.g., at least 95%, 96%, 97%, 98%, 99%, 99.5%, 99.9%, and fractions thereof) are considered as belonging to the same taxon.

DETAILED DESCRIPTION

Provided herein are compositions and methods for increasing butyrate production in a subject. In particular, provided herein are compositions, probiotic compositions, and combinations thereof that promote butyrate production in a subject.

Microbial communities in the human GI track have evolved to provide multiple services that are essential to human health. Among the most important services is the production of Short-Chain Fatty Acids (SCFAs), including butyric acid. Butyrate is essential for maintaining the integrity of the gut mucosa and thereby preventing intestinal inflammation (Marteau, *Gut* 62, 1673 (2013); Segain, J. P. et al. *Gut* 47, 397-403 (2000); Andoh, A., Bamba, T. & Sasaki, M. Physiological and anti-inflammatory roles of dietary fiber and butyrate in intestinal functions. *JPEN Parenter Enteral Nutr* 23, S70-3 (1999); Hamer, H. M. et al., *Alimentary Pharmacology & Therapeutics* 27, 104-119 (2008)), reducing the likelihood of colon cancer through regulation of colonocyte cell cycles (Hassig et al., *Chem Biol* 4, 783-9 (1997); Archer, S. et al. *Surgery* 124, 248-53 (1998); Velazquez, O. C. & Rombeau, J. L. *Adv Exp Med Biol* 427, 169-81 (1997); Lazarova, et al., *BMC Research Notes* 7, 1-8 (2014)), regulating satiety through interactions with GLP-1 (Hamer et al., supra; Yadav, et al., *J Biol Chem* 288, 25088-97 (2013)), and contributing to the regulation of hundreds of other human genes in colonocytes (Lazarova et al., supra).

SCFAs are produced when dietary fibers, found primarily in whole grains, legumes, fruits and vegetables, reach the microbiome of the large intestine (Lattimer, J. M. & Haub, M. D. *Nutrients* 2, 1266-1289 (2010)). Non-digestible plant fibers absorb and retain moisture in the colon, creating an anoxic environment that is optimal for fermentative microbes. Resistant carbohydrates in the plant material, carbohydrates that are not metabolized directly by the host, drive the metabolism of the colonic microbiome (Tremaroli, V. & Backhed, F. *Nature* 489, 242-249 (2012)). The end products of fermentation in the colon are primarily SCFAs—acetate, propionate, and butyrate. In addition to serving as a source of energy and nutrients, the gut microbiome also bolsters human immune defenses by directly outcompeting pathogens and by innervating the gut's innate immune responses (Abt, M. C. & Pamer, E. G. *Current Opinion in Immunology* 29, 16-22 (2014); Abt, M. C. & Artis, D. *Current Opinion in Microbiology* 16, 4-9 (2013); Kamada, et al., *Nature Immunology* 14, 685-690 (2013); Kamada, et al., *Nature Reviews Immunology* 13, 321-335 (2013)). Diets high in fiber, and particularly resistant carbohydrates, have also been associated with reduced incidences of obesity, type two diabetes, and cardiovascular disease (Lattimer et al., supra; Birt, D. F. et al. *Advances in Nutrition* 4, 587-601 (2013); Slavin, J. *Nutrients* 5, 1417-1435 (2013)). The gut microbiome is a primary contributing factor in the modulation of these disease states.

The amount of dietary fiber in the US is a public health concern (Millen, B. E. Scientific Report of the 2015 Dietary Guidelines Advisory Committee. (United States Department of Agriculture and the Department of Health and Human Services, 2015); Slavin, J. L. *Journal of the American Dietetic Association* 108, 1716-1731 (2008)). It is estimated that 4 percent of men and 13 percent of women have a dietary intake of fiber that meets the recommended average (25 g/day for women and 38 g/day for men) (Millen et al., supra). The shortfall in fiber consumption is between 11 and 20 grams per day. While a diet rich in vegetables, nuts, seeds and fruits is the optimal strategy for meeting the daily fiber recommendation (Millen et al., supra; Slavin et al., supra), supplementing diets with extracted plant fibers, including resistant starch, represents a viable alternative for meeting the recommended daily consumption of fiber (Millen et al., supra; Slavin et al., supra). Supplements may be particularly valuable in individuals for whom dietary modification is not feasible, when medical conditions depress appetite or are accompanied by nausea, and in individuals participating in calorie-restricted diets. Notably, these supplements are convenient as they can be readily added to water or flavored drinks.

Stimulating butyrate production with RS may occur via two pathways that differ in terms of intermediate metabolites and the microbes catalyzing the reactions (FIG. 1). A relatively small number of organisms in the gut are capable of degrading RS granules. These organisms, known as primary degraders, depolymerize the starch to make it accessible for fermentation (FIG. 1). *R. bromii* degrades RS into oligosaccharides, which it ferments to acetate. In the process, glucose, maltose, and oligosaccharides are also released and made available for fermentation by other species (Ze X, et al., *ISME J* 2012, 6(8):1535-1543). A variety of secondary fermenters can use the resulting acetate and sugars to produce butyrate. Unlike *R. bromii*, Bifidobacteria depolymerize RS and ferment it to acetate and lactate via a unique metabolic pathway known as the Bifid shunt (Scardovi V, Trovatelli L D: *Annals of Microbiology* 1965, 15:19-29). The resulting lactate and acetate can be used to produce butyrate by a relatively small number of organisms, including *Eubacteriium hallii* and *Anaerostipes hadrus* (Allen-Vercoe E, et al., *Anaerobe* 2012, 18(5):523-529; Duncan S H, et al., *Appl Environ Microbiol* 2004, 70(10):5810-5817). While other pathways are possible, it is contemplated that one or both of these two pathways are the primary mechanism for the butyrogenic effect of RS. In addition to RS, the butyrogenic effect of fructooligosaccharides in the form of inulin from chicory root were tested. Due to its solubility, inulin can be degraded by a larger number of species, including some butyrate producers (Moens F, et al., *Benef Microbes* 2017, 8(3):473-490). It was further tested whether butyrate from inulin occurs via the two-step process for RS.

Experiments described herein tested the impact of multiple dietary fiber supplements on microbiota composition and fecal SCFA concentrations in 200 healthy young adults. The butyrogenic effect of resistant potato starch were confirmed, but substantial inter-individual variation in that response was observed. It was tested whether differences in the abundance of primary degraders and secondary fermenters could explain differences in the amount of butyrate produced by each individual. It was found that much of the variation in responses were explained by changes in three species; *R. bromii*, an unclassified *Clostridum* (seq176), and *E. rectale*.

Accordingly, provided herein are compositions and methods for increasing butyrate production in a subject (e.g., in the intestine of a subject). In some embodiments, a carbohydrate source is provided to the subject in combination with a primary degrader and optionally a butyrate producer.

The present disclosure is not limited to particular sources of carbohydrate. In some embodiments, the carbohydrate comprises one or more resistant starchs. The carbohydrate or starch is provided in a purified (e.g., isolated starch or food product) or unpurified form (e.g., whole grain or fruit or vegetable), In some embodiments, the carbohydrate is one or more of corn, a corn product, potato, green banana starch, potato starch, or inulin. In some embodiments, the carbohydrate is provided as a food product or supplement comprising the carbohydrate.

The present disclosure is not limited to particular first bacteria or primary degrader. Examples include, but are not limited to *Bifidobacterium* spp., *Clostridium* seq 176, sequence 100, or *Ruminococcus bromii* (e.g., *Bifidobacterium faecale*).

In some embodiments, *Clostridium* seq 176 comprises bacteria with V4 region sequence of TACGTAGGTGGCAAGCGTTGTCCGGATTTACTGGG-CGTAAAGGGAGCGTAGGCG GATTTTTAAGTGG-GATGTGAAATACCCGGGCTCAACCTGGGTGCTG-CATTCCAAA CTGGAAGTCTAGAGTACAGGAGGG-GAAAGCGGAATTCCTAGTGTAGCGGTGAAA TGCGTAGAGATTAGGAAGAACACCAGTGGCGAAG-GCGGCTTTCTGGACTGTAAC TGACGCTGAGGC-TCGAAAGCGTGGGGAGCAAACAGG (SEQ ID NO:1) or bacteria with V4 region sequences at least 95% identical to SEQ ID NO:1 (e.g., at least 95%, 96%, 97%, 98%, 99%, 99.5%, or 99.9% identical to SEQ ID NO:1).

In some embodiments, sequence 100 comprises bacteria with V4 region sequence of TACGTAGG-GAGCGAGCGTTGTCCGGATTTACTGGGTGTAA-AGGGTGCGTAGGCG GCCGAGCAAGTCAGTTGT-GAAAACTATGGGCTTAACCCATAACGTGCAATT-GAA ACTGTCCGGCTTGAGTGAAGTAGAGGTAG-GCGGAATTCCCGGTGTAGCGGTGAA ATGCGTAGA-GATCGGGAGGAACACCAGTGGCGAAGGCGGCC-TACTGGGCTTTAA CTGACGCTGAGGCACGAAAGC-ATGGGTAGCAAACAGG (SEQ ID NO:2) or bacteria with V4 region sequences at least 95% identical to SEQ ID NO:2 (e.g., at least 95%, 96%, 97%, 98%, 99%, 99.5%, or 99.9% identical to SEQ ID NO:2).

In some embodiments, a second bacteria or butyrate producer is administered in combination with the first bacteria. The present disclosure is not limited to particular second bacteria or butyrate producers. Examples include, but are not limited to *Faecalibacterium prausnitzii, Eubacterium rectale, Roseburia* spp. (e.g., *Roseburia faecis, Roseburia intestinalis*, or *Roseburia inulinivorans*), *Eubacterium hallii*, or *Anaerostipes hadrus*.

In some embodiments, the first or second bacteria is one or more of *Eubacterium rectale* (ATCC 33656), *Faecalibacterium prausnitzii* (ATCC 27768), *Bifidobacterium longum* (ATCC 35183), *Eubacterium hallii* (ATCC 27751), *Ruminococcus bromii* (ATCC 27255), *Bifidobacterium adolescentis* (ATCC 15703), *Bifidobacterium bifidum* (ATCC 29521), *Bifidobacterium breve* (ATCC 15700), *Bifidobacterium pseudolongum* (ATCC 25526), *Bifidobacterium catenulatum* (ATCC 27539), or *Bifidobacterium angulatum* (ATCC 27670).

In some embodiments, first and/or second bacteria are isolated from fecal samples (e.g., using the method described in example 2) and then cultured in vitro.

In some embodiments, the first and/or second bacteria are formulated for oral administration. The present disclosure is not limited to particular methods of oral administration. Examples include, but are not limited to, food products, foods, nutraceuticals, nutritional supplements, capsules, etc.

In some embodiments, the first and/or second bacteria are encapsulated (e.g., alone or in combination with the carbohydrate). In some embodiments, a capsule shell that is constructed to dissolve at a predetermined pH of a target region (e.g., large intestine, small intestine, bowel, etc.) is utilized (e.g., available from Assembly Biosciences, Carmel, IN). In some embodiments, capsules also have inner and outer layers that can be engineered to dissolve at different pH levels, making it possible to use a single capsule to deliver two doses of a therapeutic to different locations in the GI tract, or to deliver two different therapeutics to different locations. In some embodiments, mucin is used in the encapsulation technology to protect against stomach acid.

In some embodiments, the first and second bacteria are provided in a single or separate capsules. In some embodiments, the carbohydrate is encapsulated with the first and/or second bacteria. In some embodiments, the carbohydrate is provided separately. In some embodiments, the carbohydrates is provided as a food or food product and the first and/or second bacteria are microencapsulated in or on the food or food product.

In some embodiments, the carbohydrate and/or the first and second bacteria are formulated for rectal administration (e.g., as a suppository). Further formulations are described below.

In some compositions embodiments, compositions are formulated in pharmaceutical compositions. The bacteria of embodiments of the disclosure may be administered alone or in combination with pharmaceutically acceptable carriers or diluents, and such administration may be carried out in single or multiple doses.

Compositions may, for example, be in the form of tablets, resolvable tablets, capsules, bolus, drench, pills sachets, vials, hard or soft capsules, aqueous or oily suspensions, aqueous or oily solutions, emulsions, powders, granules, syrups, elixirs, lozenges, reconstitutable powders, liquid preparations, creams, troches, hard candies, sprays, chewing-gums, creams, salves, jellies, gels, pastes, toothpastes, rinses, dental floss and tooth-picks, liquid aerosols, dry powder formulations, HFA aerosols or organic or inorganic acid addition salts.

The pharmaceutical compositions of embodiments of the disclosure may be in a form suitable for oral or rectal administration. Depending upon the disorder and patient to be treated and the route of administration, the compositions may be administered at varying doses.

For oral administration, bacteria of embodiments of the present disclosure may be combined with various excipients. Solid pharmaceutical preparations for oral administration often include binding agents (for example syrups, acacia, gelatin, tragacanth, polyvinylpyrrolidone, sodium lauryl sulphate, pregelatinized maize starch, hydroxypropyl methylcellulose, starches, modified starches, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone and sodium alginate), disintegrants (such as starch and preferably corn, potato or tapioca starch, alginic acid and certain complex silicates, polyvinylpyrrolidone, gelatin, acacia, sodium starch glycollate, microcrystalline cellulose, crosscarmellose sodium, crospovidone, hydroxypropyl methylcellulose and hydroxypropyl cellulose), lubricating agents (such as magnesium stearate, sodium lauryl sulfate, talc, silica polyethylene glycol waxes, stearic acid, palmitic acid, calcium stearate, carnuba wax, hydrogenated vegetable oils, mineral oils, polyethylene glycols and sodium stearyl fumarate) and fillers (including high molecular weight polyethylene glycols, lactose, calcium phosphate, glycine magnesium stearate, starch, rice flour, chalk, gelatin, microcrystalline cellulose, calcium sulphate, and lactitol). Such preparations may also include preservative agents and anti-oxidants.

Liquid compositions for oral administration may be in the form of, for example, emulsions, syrups, or elixirs, or may be presented as a dry product for reconstitution with water or other suitable vehicle before use. Such liquid compositions may contain conventional additives such as suspending agents (e.g. syrup, methyl cellulose, hydrogenated edible fats, gelatin, hydroxyalkylcelluloses, carboxymethylcellulose, aluminium stearate gel, hydrogenated edible fats) emulsifying agents (e.g. lecithin, sorbitan monooleate, or acacia), aqueous or non-aqueous vehicles (including edible oils, e.g. almond oil, fractionated coconut oil) oily esters (for example esters of glycerine, propylene glycol, polyethylene glycol or ethyl alcohol), glycerine, water or normal saline; preservatives (e.g. methyl or propyl p-hydroxybenzoate or sorbic acid) and conventional flavouring, preservative, sweetening or colouring agents. Diluents such as water, ethanol, propylene glycol, glycerin and combinations thereof may also be included.

Other suitable fillers, binders, disintegrants, lubricants and additional excipients are well known to a person skilled in the art. In some embodiments, compositions include one or more of mucin, antioxidants, reductants, or redox-active compound (e.g., to protect bacteria).

In some embodiments, bacteria are spray-dried. In other embodiments, bacteria re-suspended in an oil phase and are encased by at least one protective layer, which is water-soluble (water-soluble derivatives of cellulose or starch, gums or pectins; See e.g., EP 0 180 743, herein incorporated by reference in its entirety).

In some embodiments, compositions are provided as a nutritional or dietary supplement. In some embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The dietary supplement may comprise one or more inert ingredients, especially if it is desirable to limit the number of calories added to the diet by the dietary supplement. For example, the dietary supplement may also contain optional ingredients including, for example, herbs, vitamins, minerals, enhancers, colorants, sweeteners, flavorants, inert ingredients, and the like. For example, the dietary supplement may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), *spirulina*, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In some embodiments, compositions are provided as nutritional supplements (e.g., energy bars or meal replacement bars or beverages). The nutritional supplement may serve as meal or snack replacement and generally provide nutrient calories. In some embodiments, the nutritional supplements provide carbohydrates, proteins, and fats in balanced amounts.

Sources of protein to be incorporated into the nutritional supplement are any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. Guidance to the amounts or ingredients can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In some embodiments, the nutritional supplement contains natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In one embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

In some embodiments, compositions are provided as food products, prepared food products, or foodstuffs comprising carbohydrate and bacteria as described above. For example, in some embodiments, beverages and solid or semi-solid foods are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

In some embodiments, the present disclosure provides kits, pharmaceutical compositions, or other delivery systems for use in increasing butyrate levels in an animal and/or identifying animals in need of treatment with the compositions and methods described herein. The kit may include any and all components necessary, useful or sufficient for research or therapeutic uses including, but not limited to, one or more bacteria, carbohydrate sources, pharmaceutical carriers, PCR primers, reagents, enzymes, buffer, and additional components useful, necessary or sufficient for increasing butyrate levels in an animal or identifying animals in need of treatment with the compositions described herein. In some embodiments, kits include directions for performing diagnostic assays and/or determining a treatment course of action based on the results of the diagnostic assay. In some embodiments, the kits provide a sub-set of the required components, wherein it is expected that the user will supply the remaining components. In some embodiments, the kits comprise two or more separate containers wherein each container houses a subset of the components to be delivered.

Optionally, compositions and kits comprise other active components in order to achieve desired therapeutic effects and/or perform diagnostic assays.

The compositions and methods described herein find use in increasing butyrate concentrations in the intestine of a subject (e.g., human). In some embodiments, the butyrate is increased relative to a control level. The present disclosure is not limited to particular reference or control levels. In some embodiments, control level is the level in an individual not administered the carbohydrate and the first and second bacteria, the level in an individual diagnosed with a disease or conditions related to low butyrate levels, or a sub-optimal level of butyrate.

In some embodiments, the disease or condition includes, but is not limited to, type II diabetes, metabolic syndrome, obesity, neurological disorders (See e.g., Bourassa et al., *Neuroscience Letters* 625 (2016) 56-63; herein incorporated by reference in its entirety), cancer, or graft versus host disease (e.g., resulting from transplantation, e.g., bone marrow transplantation).

In some embodiments, compositions described herein are administered one or more times (e.g., daily, multiple times a day, multiple times a week, multiple times a month, etc.) for a period of time (e.g., weeks, months, years, indefinitely). In some embodiments, compositions are administered in order to obtain and maintain a desired outcome (e.g., level of butyrate in the intestine, reduction in symptoms of a disease or condition, etc.).

In some embodiments, the butyrate levels of an individual are assayed one or more times prior to or during treatment (e.g., in order to increase the level of butyrate in the intestine). In some embodiments, the treatment is altered (e.g., change in dosage or specific bacteria and carbohydrate administered) in response to the level of butyrate. For example, if butyrate levels remain below a desired level or level of increase, the amount or type of bacteria and/or carbohydrate can be altered. The levels of butyrate are then assayed again to assess the new treatment.

In some embodiments, the microbiome of a subject is tested prior to treatment. For example, in some embodiments, the presence of one or more bacteria (e.g., *Bifidobacterium* spp., *Clostridium* seq 176, sequence 100, *Ruminococcus bromii*, *Faecalibacterium prausnitzii*, *Eubacterium rectale*, *Roseburia* spp., *Eubacterium halii*, or *Anaerostipes hadrus*) is determined and used to provide and/or administer a treatment course of action. For example, in some embodiments, individuals found to have one or more of the described bacteria (e.g., sequence 100 and/or *Ruminococcus bromii*) are administered a resistant starch alone. In some embodiments, individuals found to be lacking a first and/or second bacteria as described herein are administered the bacteria they are lacking and a resistant starch.

EXAMPLES

Example 1

Methods
Study Participants

Study participants were recruited through the Authentic Research Sections of the introductory biology laboratory course at the University of Michigan (BIO173). Individuals with self-reported history of inflammatory bowel syndrome, inflammatory bowel disease, or colorectal cancer were excluded from the study. All participants gave written, informed consent prior to participating in the study. Participants under the age of 18 were granted permission by a parent or legal guardian. Participants ranged in age from 17 to 29, with a median age of 19.

Study Design

During the first week of the study (hereafter referred to as the "before" supplementation period) each participant collected 3 to 4 fecal samples on separate days. During the second week, participants underwent a 4 to 7 day transition phase, in which they started by consuming a low dose of the supplement and transitioned up to the full dose. No fecal samples were collected during the transition phase. In the third week of the study (hereafter referred to as the "during" supplementation period), participants continued taking the full dose of their assigned supplement until they had collected 3 to 4 fecal samples on separate days.

Dietary Supplements

Four different supplements were tested in this study; resistant potato starch (Bob's Red Mill, Milwaukie, OR), Hi-Maize 260 resistant corn starch (manufactured by Ingredion Inc., Westchester, IL and distributed by myworldhut.com), inulin isolated from chicory root (Swanson), and accessible corn starch (Amioca corn starch, Skidmore Sales and Distribution, West Chester OH). Both the potato starch and Hi-Maize supplements were approximately 50% RS (type 2) by weight. Subjects consumed a total of 40 to 48 grams of the RS supplements per day. The inulin supplement, which was presumed to be predominantly resistant to human amylases, was consumed at half the dose of the potato and Hi-Maize (20 g/day) to provide approximately the same amount of microbiota-accessible carbohydrate. The accessible starch supplement was also given at half the dose of the potato and Hi-Maize (20 g/day) to provide approximately the same amount of host-accessible carbohydrates. Consumption of the supplements was split into two half doses per day. Participants were provided with a shaker bottle to aid in mixing the supplement with a beverage, however they were permitted to consume the supplement with any type of food or beverage, provided that the supplement was never heated. Aside from the supplement, participants maintained their normal diet throughout the study.

Fecal Collection

Fecal samples were collected by participants as described previously (Venkataraman A, et al., *Microbiome* 2016, 4(1): 33). Participants collected approximately half a gram of fecal material into an OMNIgene-Gut® (DNA Genotek) collection kit, following manufacturer instructions. Collection tubes were transferred to a −20° C. freezer within 24 hours of collection and stored at −20° C. until thawed for DNA and metabolite extractions. Collection tubes were weighed before and after fecal collection, to determine the weight of the fecal material collected.

SCFA Quantification

To extract SCFAs, 1 ml of fecal suspension was transferred into a 96-well collection plate and centrifuged at 4,500×G for 15 minutes at 4° C. Supernatant fractions were successively filtered through 1.20, 0.65, and 0.22 µm 96-well filter plates at 4° C. Filtrates were transferred to 1.5 ml screw cap vials with 100 µl inserts in preparation for analysis by high-performance liquid chromatography (HPLC). Samples were analyzed in duplicate and loaded in a randomized order. Quantification of SCFAs was performed using a Shimadzu HPLC system (Shimadzu Scientific Instruments, Columbia, MD) that included an LC-10AD vp pump A, LC-10AD vp pump B, degasser DGU-14A, CBM-20A, autosampler SIL-10AD HT, Column heater CTO-10A (C) vp, UV detector SPD-10A(V) vp, RID-10A detector and an Aminex HPX-87H column (Bio-Rad Laboratories, Hercules, CA). A mobile phase of 0.01 N $H_2SO_4$ flowing at a rate of 0.6 ml per minute was used. The sample injection volume was 10 µl. Concentrations were calculated using a cocktail of short chain organic acids standards at concentrations of 20, 10, 5, 2.5, 1, 0.5, 0.25, and 0.1 mM. Concentrations were normalized to the wet weight of fecal material. After correcting the baseline of chromatographs, the quality of peaks was assessed using peak width, relative retention time, and 5% width. Peaks that fell outside predetermined cutoffs for each measurement were removed.

16S rRNA Gene Sequencing

DNA was extracted from 250 µl of fecal suspension using the 96-well MagAttract PowerMicrobiome DNA Isolation kit (Qiagen) and an EpMotion 5075 automated pipetting system (Eppendorf). The V4 region of the bacterial 16S rRNA gene was amplified and sequenced as described previously using 2×250 base pair paired end kits on the Illumina MiSeq sequencing platform (Kozich J J, et al., *Appl Environ Microbiol* 2013, 79(17):5112-5120). Samples were split between 8 separate DNA sequencing runs. Sequences were curated using the mothur software package as described previously (Kozich et al., supra; Schloss P D, et al., *Appl Environ Microbiol* 2009, 75(23):7537-7541). Briefly, paired end reads were merged into contigs, screened for sequencing errors, and aligned to the SILVA bacterial SSU reference database. Aligned sequences were screened for chimeras and classified using the Ribosomal Database Project database. Sequences classified as mitochondria, chloroplasts, or archaea were removed. Sequences of interested were further identified using BLAST to align against the 16S rRNA sequences database. Unless stated otherwise, species designations indicate 100% identity to a single species in the database.

Sequences were not clustered into operational taxonomic units after discovering that several taxa of interest, with very different responses to the dietary supplements, would be clustered into a single OTU even at the 99% identity. For example, *Bifidobacterium longum* and *B. faecale* have varying abilities to degrade RS, but the V4 region of the 16S rRNA gene in these species is 99.6% identical. Combining sequences corresponding to these species masks a biological pattern that is readily apparent when considering the unique sequences. However, the high sequence identity in the V4 region of Bifidobacteria makes it impossible to resolve all individual species. *B. adolescentis* and *B. faecale* have identical V4 regions, as do *B. longum* and *B. breve*. A third group, *B. catenulatum*, *B. pseudocatenulatum*, and *B. kashiwanohense*, also share identical V4 regions. For all other species of interest, a single sequence was identified that was specific to each species. To avoid analysis of spurious sequences, the analysis was limited to the 500 most abundant sequences, which accounted for 71% of the approximately 70 million curated sequencing reads. The number of sequences per sample was rarified to 3000 sequence to prevent biases from uneven sampling.

Statistical Analyses

All statistical analyses were performed using R (version 3.2.4) via RStudio (version 1.0.136). Changes in the overall community structure in response to supplements were assessed using PERMANOVA on Bray-Curtis distances stratified by subject. For other comparisons of the relative abundance of microbiota, the average relative abundance within each individual at each time point was used, yielding a single average community structure for each individual before and during supplementation. Organisms that responded most strongly to each supplement were identified using one-tailed paired Wilcoxon-tests on the average abundances in each subject before and during supplementation. The sequences with the largest average increase and that increased in at least 10% of individuals consuming a particular supplement were investigated further. To determine whether there was a significant change in SCFA concentration from before to during fiber supplementation, repeated measures ANOVAs was performed on SCFA concentrations in all fecal samples from individuals consuming each supplement. For other analyses, the median SCFA concentration within each individual at each time point was used.

Results

The impact of each fiber supplement on the concentration of SCFAs in the feces was examined. Dietary supplementation with resistant potato starch increased butyrate concentrations by an average of 30% ($p<0.001$) and acetate by an average of 22% ($p=0.001$, Table 1). However, the response was highly variable between individuals: the median concentration of butyrate increased in 64% of individuals and was either constant or decreased in the remaining 36%. Inulin also increased butyrate concentrations, but by a smaller extent (17%) and with less certainty ($p=0.06$). The variability with inulin was similar to dietary supplementation with potato starch, median butyrate concentrations increased in 60% of the individuals consuming inulin. There were no measureable changes in the concentration of any of the SCFAs in the groups of individuals whose diet was supplemented with either Hi-Maize 260® ($p=0.82$) or accessible starch ($p=0.34$).

Figure 6:
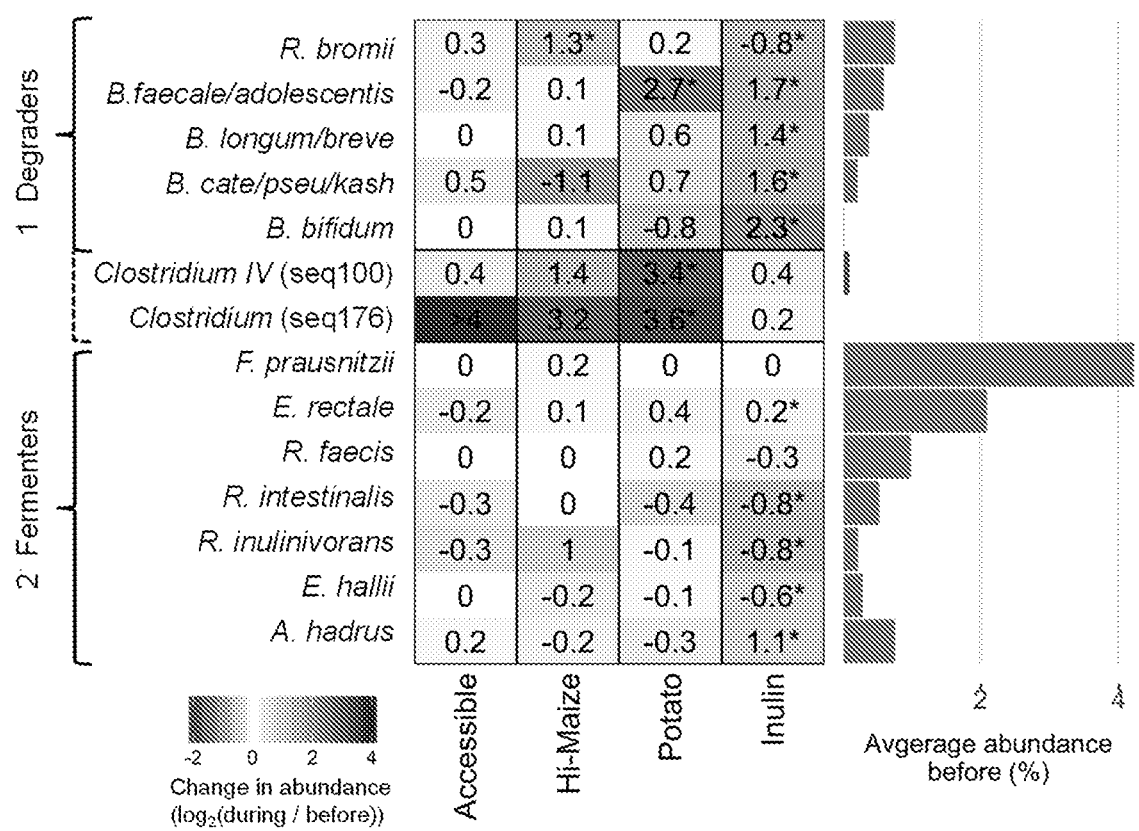
FIG. 6 shows a heatmap showing the fold change in relative abundance of species of interest in response to supplements (* $p<0.05$, paired Wilcoxon test). Bar plot to the right shows the average relative abundance of each species prior to fiber supplementation.

Given the variable responses to supplements among individuals, it was determined how the composition of the microbiota changed in response to each supplement, particularly those species predicted to be important for RS degradation. Both the potato starch and inulin significantly altered the overall structure of the community (PERMANOVA, $p=0.001$ and $p=0.002$, respectively), but the accessible starch and Hi-Maize did not ($p=1$ and $p=0.65$, respectively). None of the supplements significantly changed the alpha diversity (repeated measures ANOVA on inverse Simpson index, all $p>0.05$). *R. bromii* and several species of Bifidobacteria are known to degrade RS and were expected to increase in response to the RS supplements. On average the Hi-Maize supplement resulted in a 2.5-fold increase in *R. bromii* ($p<0.001$), but no significant changes in any of the Bifidobacteria (FIG. 6). In contrast, RS from potato resulted in a 6.5-fold increase in the *B. faecale/adolescentis* sequence ($p<0.001$), but no significant change to any of the other Bifidobacteria (FIG. 2A, 6). *R. bromii* increased in a subset of individuals (FIG. 2A), but not for the group as whole ($p=0.72$). Each of the four most abundant Bifidobacterium sequences significantly increased in response to inulin, while the relative abundance of R. bromii decreased (FIG. 6, all p<0.05).

Figure 2:
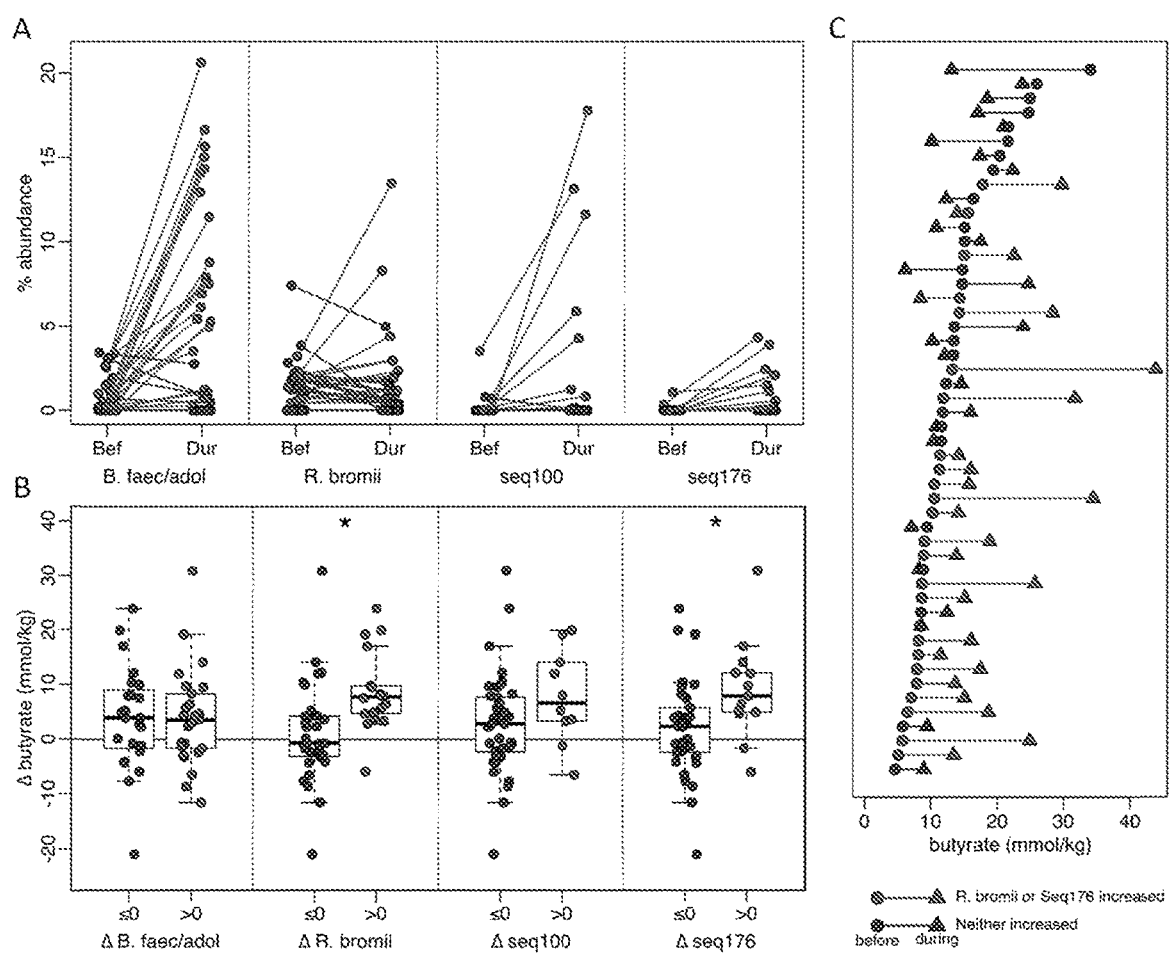
FIG. 2 shows an increase in primary degraders associated with higher A butyrate. (A) Average relative abundance of putative primary degraders in each individual before and during potato starch supplementation. (B) Change in fecal butyrate in individuals grouped based on whether a particular sequence increased ($\Delta>0$) or did not increase ($\Delta\leq0$) in relative abundance (* $p<0.05$, t-test). (C) Butyrate concentrations for each individual before (circles) and during (triangles) potato starch supplementation. Subjects sorted by initial butyrate concentration.

In addition to the species that were predicted would respond to the supplements, an increase in the relative abundance of two unclassified sequences was observed in response to dietary supplementation with potato starch. The first, referred to as seq100, was classified as a member of Clostridium cluster IV within the Ruminococcaceae family. It was detected in 11 of the 50 individuals who consumed potato starch, increasing by an average of 10-fold and exceeding 10% relative abundance in several individuals (FIG. 2A, FIG. 6). A second unclassified sequence (seq176) also increased by approximately 10-fold in individuals consuming potato starch. Seq176 was 99% identical to Clostridium chartatabidum, a rumen isolate shown to degrade a variety of dietary fibers, though not starch (Kelly W J, et al., Arch Microbiol 1987, 147(2):169-173).

Based on the model (FIG. 1), it was hypothesized that the butyrate-stimulating effect of potato starch is associated with the increased abundance of a primary degrader, indicating degradation of the substrate. Neither an increase in B. faecalis/adolescentis nor seq100 was associated with a greater increase in butyrate (FIG. 2B). In contrast, increases in either R. bromii or seq176 were each associated with a greater increase in butyrate (p=0.025 and p=0.0024, FIG. 2B). On average, there was a 9.6 mmol/kg increase in fecal butyrate in individuals in which either R. bromii or seq176 increased in abundance, compared to a decrease of 1.3 mmol/kg in individuals in whom neither sequence increased (FIG. 2C). Furthermore, the presence or absence R. bromii prior to supplementation could be used to classify individuals as responders (increased butyrate in response to supplement) or non-responders (decreased butyrate) with 74% accuracy. The baseline abundance of seq176 was a poor predictor because it was below the limit of detection (~0.008% abundance) in all but five individuals prior to supplementation. It is contemplated that the presence of these two organisms can predict whether an individual will respond to resistant potato starch with increased butyrate.

Figure 3:
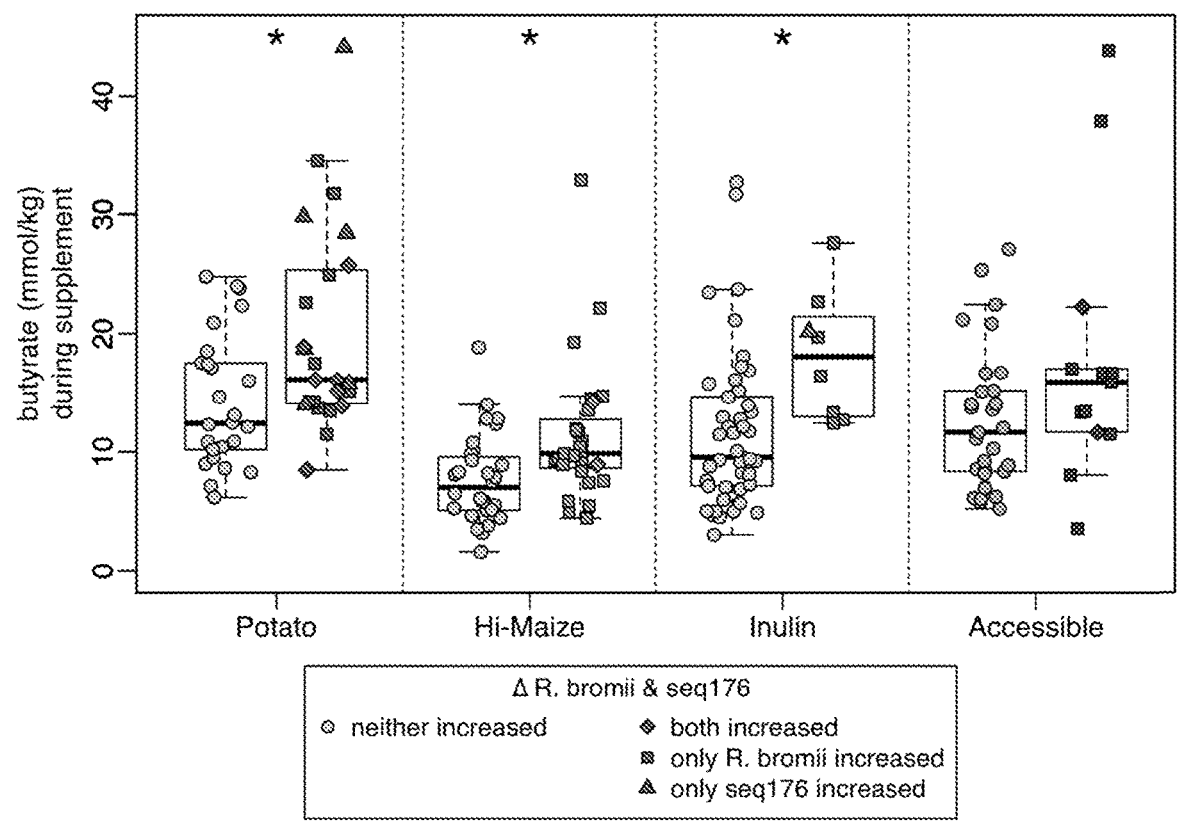
FIG. 3 shows an increase in *R. bromii* or seq176 is associated with higher butyrate concentration during supplement consumption. (* $p<0.05$, t-test).
Figure 7:
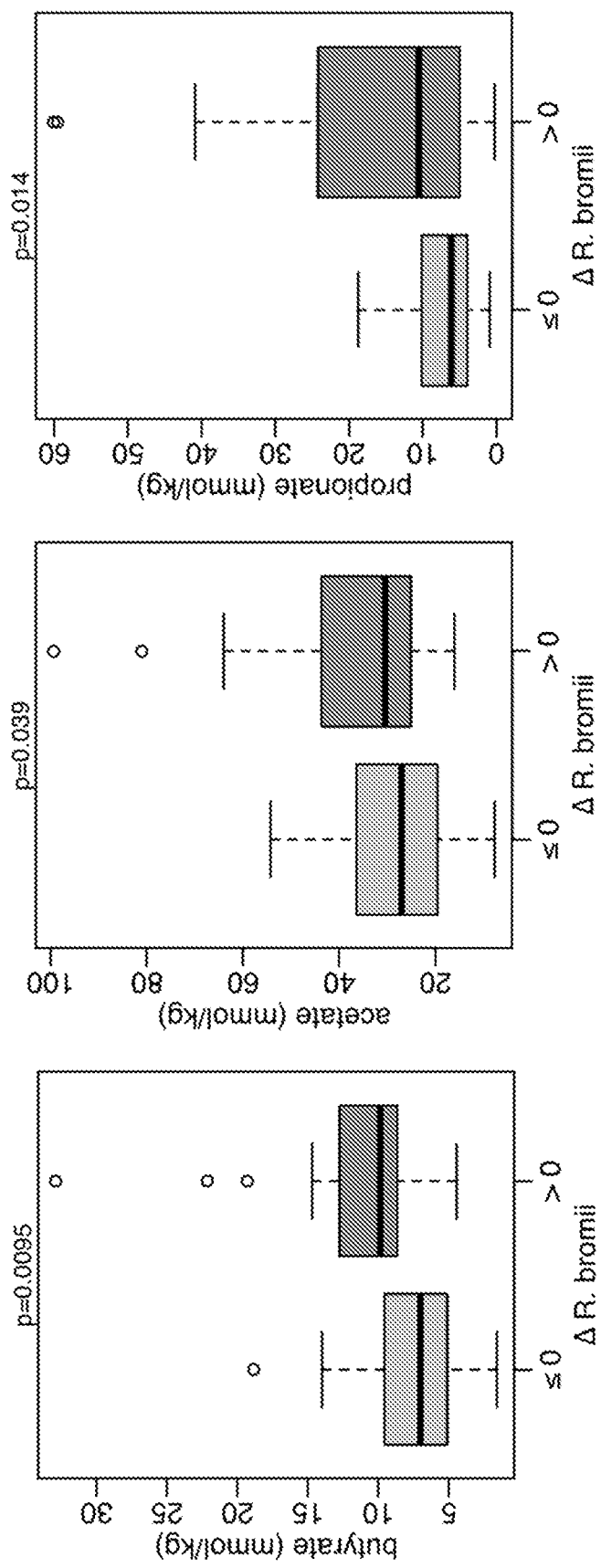
FIG. 7 shows SCFA concentrations form individuals with or without an increase in *R. bromii* during Hi-Maize consumption.
Figure 8:
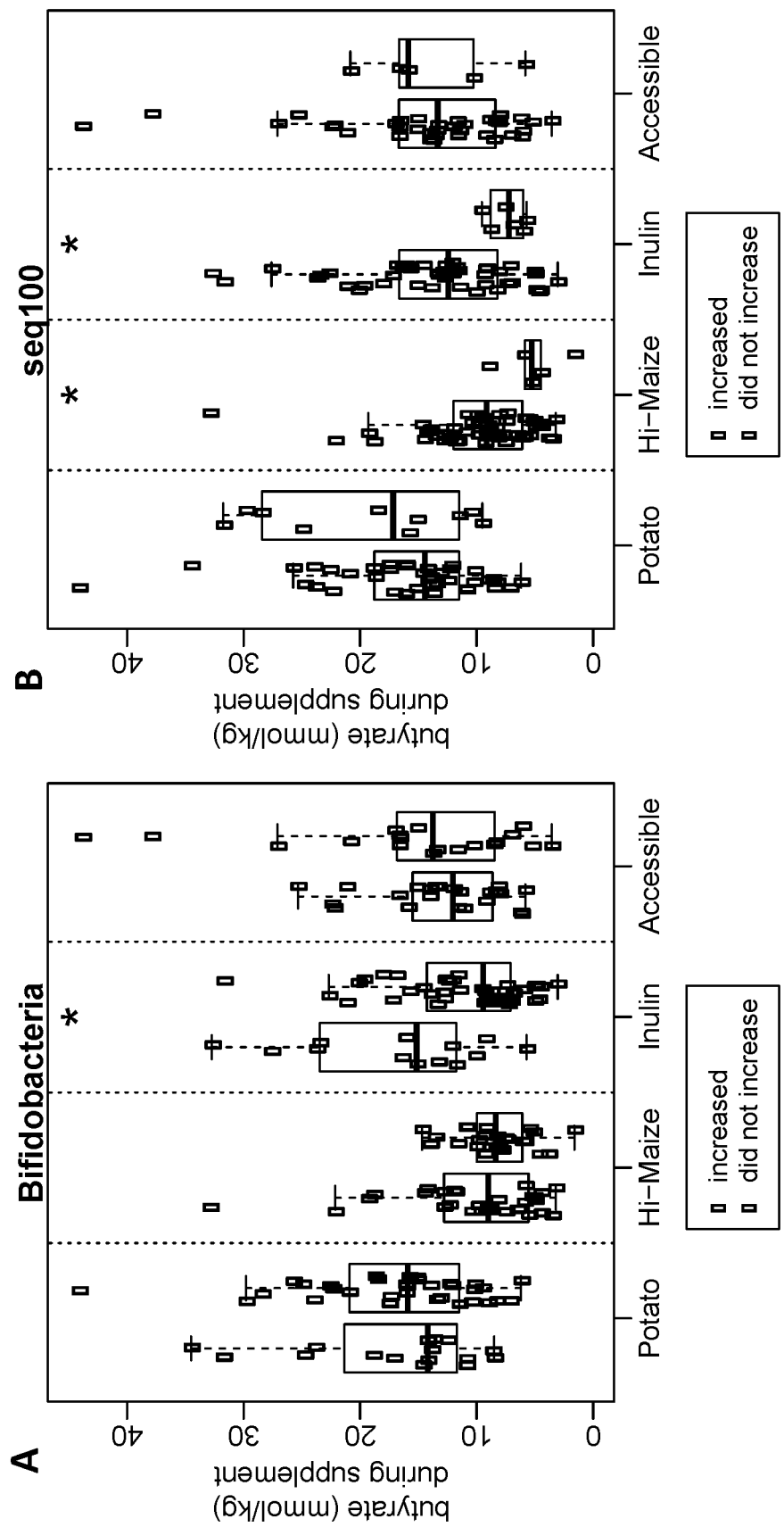
FIG. 8 shows that an increase in *B. faecale/adolescentis* or seq100 is not associated with higher butyrate concentrations. Dark markers indicate individuals in whom that sequence increased in abundance. Light markers indicate individuals in whom that sequence did not increase. (* $p<0.05$, t-test)
Figure 9:
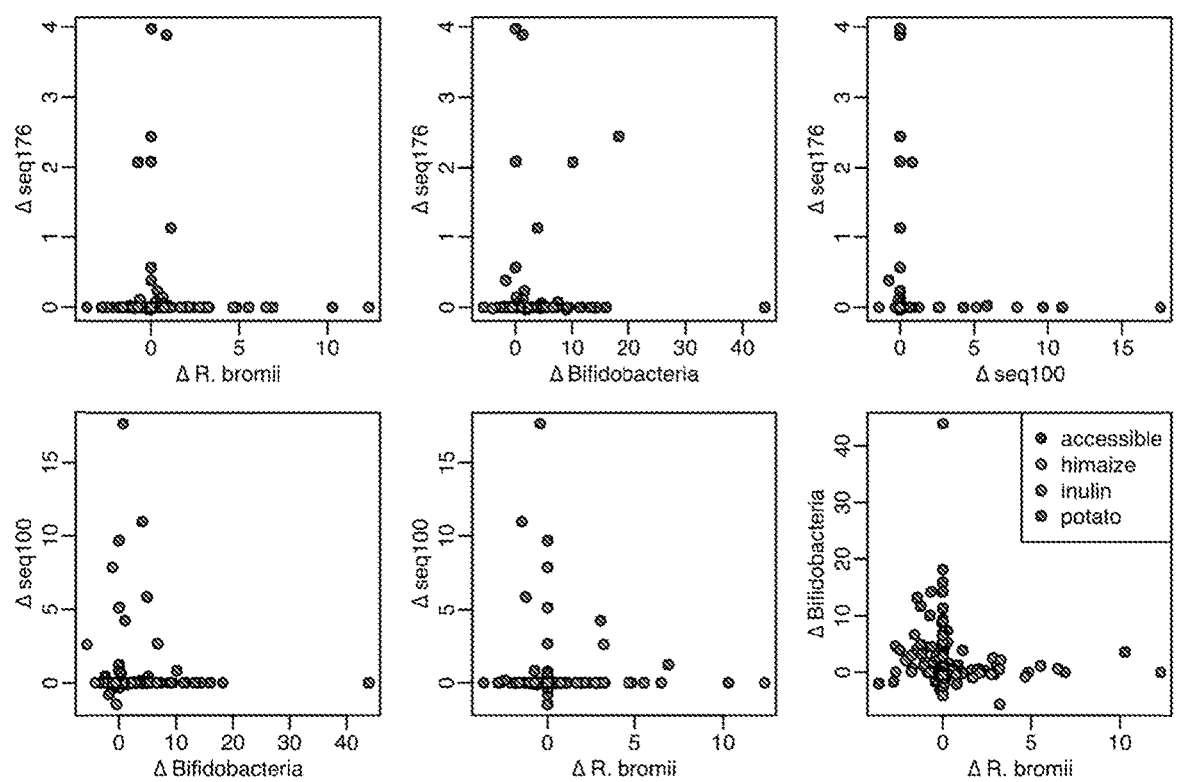
FIG. 9 shows a pairwise comparisons of the change in abundance of primary degraders.

Following the observations from the potato starch treatment group, it was tested whether a similar association between R. bromii, seq176, and butyrate existed in individuals who consumed the other substrates. For all three fiber supplements, an increase in R. bromii or seq176 was associated with higher butyrate concentrations during supplementation (FIG. 3). Only in the accessible starch group was this association not observed. A comparatively small number of individuals had increased seq176 while consuming Hi-Maize or inulin, so the association with higher butyrate was driven primarily by R. bromii for those two supplements. An increase in R. bromii was also associated with higher acetate, propionate, and total SCFA concentrations during Hi-Maize supplementation (all p<0.05, FIG. 7). As with potato starch, an increase in Bifidobacteria or seq100 was not associated with higher butyrate concentration while consuming the other supplements. In fact, an increase in Bifidobacteria was associated with significantly lower butyrate concentrations during inulin consumption (FIG. 8). An increase in seq100 was associated with lower butyrate concentrations during either inulin or Hi-Maize consumption.

Figure 4:
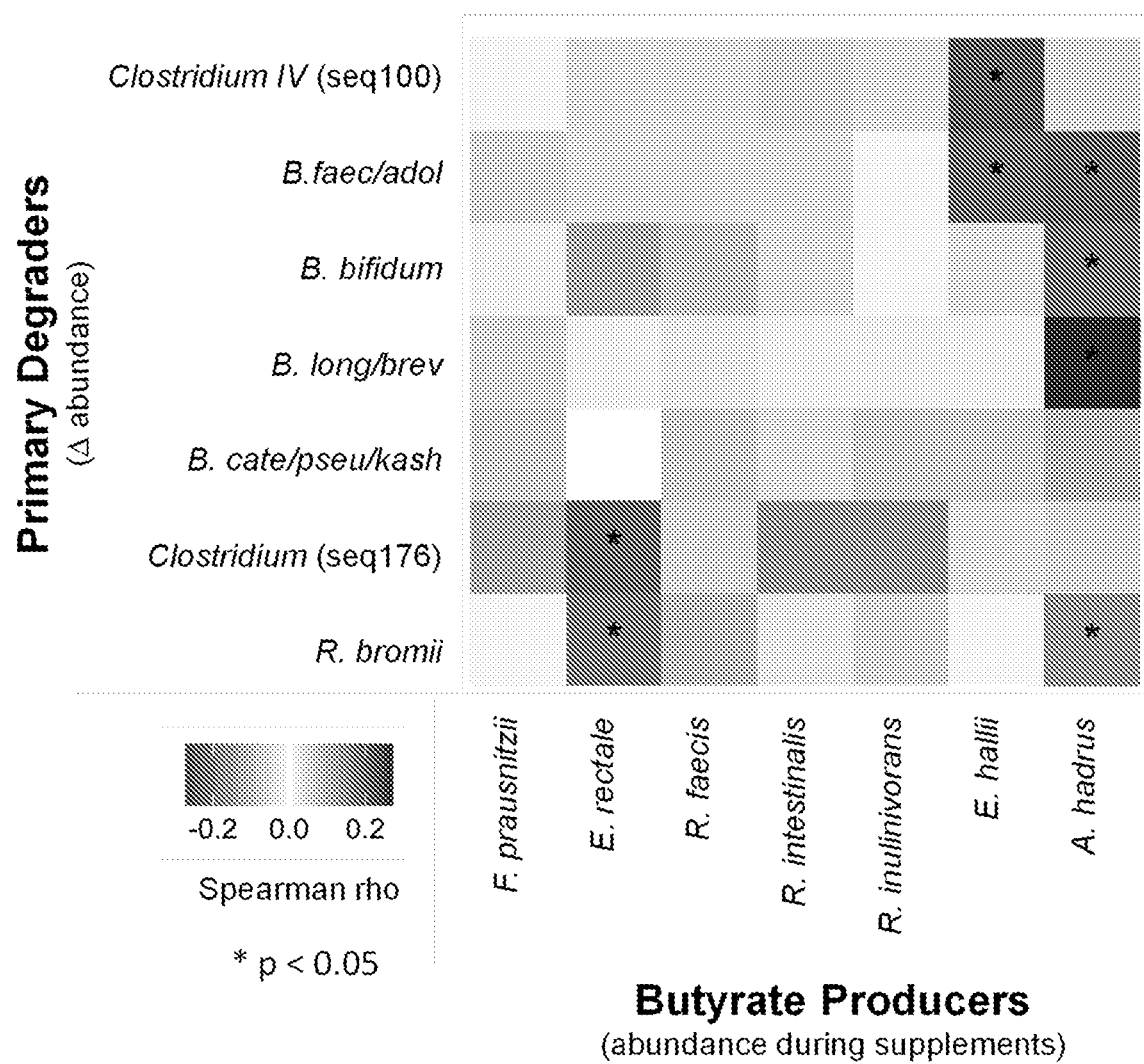
FIG. 4 shows a heatmap showing correlations between the abundance of secondary fermenters and the change in abundance of primary degraders. Correlations calculated using multiple fiber supplements. Rows sorted based on hierarchical clustering.

Butyrate is not a major end product of R. bromii metabolism. Therefore, the increase in R. bromii is not sufficient to explain its association with higher butyrate concentrations. Based on the model (FIG. 1), it was expected that the increase in primary degraders leads to greater abundance of secondary fermenters during the supplementation period. To test this, the change in abundance of each putative primary degrader was correlated with the relative abundance of several of the most common butyrate producers in the cohort (FIG. 4). Changes in R. bromii and seq176 were positively correlated with the abundance of E. rectale, consistent with the model and with previous reports that R. bromii and E. rectale are associated, both physically and metabolically (Ze X, et al., ISME J 2012, 6(8):1535-1543; Leitch E C, et al., Environ Microbiol 2007, 9(3):667-679). The abundance of E. rectale was also correlated with the concentration of butyrate during consumption of the fiber supplements (Spearman rho=0.32, p<0.001, FIG. 5A), which may explain the higher butyrate in individuals in whom R. bromii or seq176 increased. The changes in Bifidobacteria were positively correlated with lactate-utilizing butyrate producers, A. hadrus and E. hallii.

Figure 5:
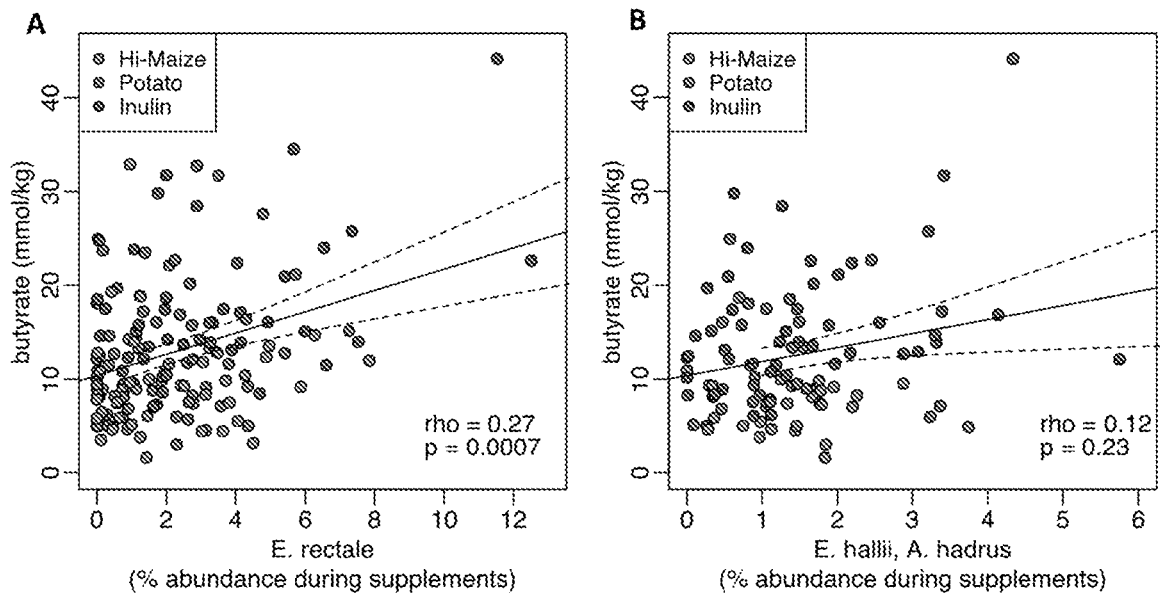
FIG. 5 shows scatter plots of butyrate concentrations and the abundance of *E. rectale* (A) or *E. hallii* and *A. hadrus* (B) during fiber supplementation.

However, the abundance of these two butyrate producers was not correlated with butyrate concentrations during fiber supplementation (FIG. 5B). These findings corroborate the model that lactate-utilizing butyrate producers respond with Bifidobacteria, while butyrate producers using acetate and glucose increase with R. bromii.

It is contemplated that the presence of R. bromii or seq176 can be used to predict whether an individual will benefit from a resistant potato starch supplement. In some embodiments, individuals without R. bromii are given probiotic supplementation to induce a butyrogenic response to RS. It is contemplated that there is a synergistic effect of combining potato starch with R. bromii and/or E. rectale to maximize the butyrogenic effect of the supplement. In contrast, individuals with high levels of Bifidobacteria may be less likely to respond to inulin with increased butyrate. In which case, a different supplement may be used.

TABLE 1

| Substrate | Butyrate | | | | Acetate | | | | Propionate | | | |
|---|---|---|---|---|---|---|---|---|---|---|---|---|
| | before (mean ± SD) | during (mean ± SD) | % Change | p-value | before (mean ± SD) | during (mean ± SD) | % Change | p-value | before (mean ± SD) | during (mean ± SD) | % Change | p-value |
| Accessible (n = 42) | 13 ± 6.2 | 14 ± 8.2 | +8% | 0.34 | 41 ± 17 | 40 ± 15 | −2% | 0.84 | 10 ± 6.0 | 9 ± 6.4 | −8% | 0.47 |
| Hi-Maize (n = 55) | 10 ± 4.7 | 10 ± 5.2 | −3% | 0.82 | 37 ± 17 | 33 ± 17 | −11% | 0.10 | 12 ± 14 | 12 ± 13 | +1% | 0.81 |
| Potato (n = 50) | 13 ± 6.0 | 17 ± 7.7 | +30% | <0.001 | 46 ± 22 | 56 ± 26 | +22% | 0.0011 | 10 ± 7.3 | 9 ± 5.4 | −12% | 0.39 |
| Inulin (n = 53) | 11 ± 6.1 | 13 ± 6.9 | +17% | 0.060 | 38 ± 17 | 41 ± 20 | +8% | 0.39 | 10 ± 9.8 | 13 ± 15 | +28% | 0.31 |

Example 2

This example describes methods of isolating bacteria from fecal samples. The HIGHLIGHT workflow involves preparation of the fecal sample, staining with Redox Sensor Green to identify viable microbes, fluorescence activated cell sorting (FACS), incubation under anoxic conditions, monitoring growth with spectrophotometry, sequencing for identity, and archiving for future use. A key facet to the methodology is the maintenance of anaerobic conditions when attempting to culture gut microbiota.

Media Preparation

YCFA and RCM liquid media were prepared two days in advance and stored in an anoxic Coy chamber for two days to equilibrate. Four 96-well plates (FisherScientific BioLite 96-well Multidish) of media were prepared with 150 μL of liquid media into each well. Two 96-well plates were prepared using YCFA and two were prepared using RCM.

Sample Preparation

A fecal sample was obtained the morning of the cell sort from a healthy donor in a 9 mL dilution blank tube (Anaerobe Systems Catalog #AS-908) as well as in a storage tube (DNA Genotek OMNIgene GUT OMR-200). The storage tube was frozen at −80° Celsius and the dilution blank sample was introduced to the anaerobic Coy chamber. The sample was shaken for homogenization and filtered through a 40 μm cell strainer (FisherScientific Falcon Cell Strainers). The filtered sample was diluted 100-fold into each of the three utilized media (YCFA, RCM, and dilution blank buffer).

One mL of each sample type was transferred to four 5 mL polypropylene round-bottom tubes (BD Falcon Catalog #352063) for a total of 12 sample tubes for bulk sorting. A further two samples of the YCFA and RCM preparations were transferred by 1 mL to the 5 mL polypropylene round-bottom tubes for use in single cell sorting. One μL of RedoxSensor Green (RSG) was added to half of the tubes for bulk sorting, yielding two tubes of each media type with dye and two tubes without. For single cell sorting, 1 μL of RSG was added to half of the tubes yielding one tube per each media type with dye and one without, to serve as a negative. The dye was added approximately 15 minutes before the FACS appointment time. All samples and 96-well plates were prepared for transport to the FACS facility in individual BD GasPak EZ Pouches to preserve anoxic headspace.

Cell Sorting

The Sony iCyt SY3200 Cell Sorter system was utilized for single cell and bulk sorting by a technician from the University of Michigan Medical School Flow Cytometry Core. Samples were analyzed using the SY3200's 488 nm laser with a 525/50 filter. Events were gated based on an FSC width between 14,000 and 24,000, which encompassed approximately 92% of the total event population for all samples. An additional gating was applied to SSC Width from 15,000 to 28,000, which encompassed approximately 67% of the total event population for all samples. The sheath fluid consisted of a 5% NaCl solution prepared by the Flow Cytometry Core.

The single cell sorting was undertaken first, with the machine calibrated to drop a single particle into each well of a 96-well plate, except for the last 3 wells (H10-H-12), which were left as medium blanks. A non-fluorescing sample of the fecal slurry was loaded before the fluorescent fecal slurry to determine background fluorescence. Gating for sorting fluorescent particles was defined to encompass all events with a 525/50 488 area (fluorescent profile) greater than events observed in the non-fluorescent sample. A single fluorescent cell was sorted from the YCFA fecal slurry with RSG into wells A1 through H9 on two 96-well plates of YCFA, and repeated with the RCM sample into 96-well plates containing RCM. To avoid oxygen exposure all plates and samples were left in BD GasPak EZ Pouches until ready to be processed. When a 96-well plate finished sorting, it was immediately placed back into a pouch with two carbon catalysts (BD GasPak EZ Anaerobe Container System REF #260678) to remove oxygen. The four sorted 96-well plates were transported to an anaerobic Coy chamber and incubated at 37° C. in individual pouches with catalysts removed.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A method of increasing butyrate levels in the intestine of a subject, comprising:
   a) assaying a sample from a subject for the presence of *Clostridium* seq 176 and/or *Ruminococcus bromii*; and
   b) administering a composition comprising a potato starch and one or both of *Clostridium* seq 176 and/or *Ruminococcus bromii* to a subject lacking said *Clostridium* seq 176 and/or Ruminococcus bromii, wherein said composition comprises said *Clostridium* seq 176 and/or Ruminococcus bromii that the subject lacks.

2. The method of claim 1, wherein said composition is a capsule.

3. The method of claim 1, wherein said composition is administered orally.

4. The method of claim 1, wherein said composition is administered rectally.

5. The method of claim 4, wherein said composition is a suppository.

6. The method of claim 1, wherein said subject is a human.

7. The method of claim 1, wherein the increased level of butyrate is increased relative to a control selected from the group consisting of the level in an individual not administered said composition, the level in an individual diagnosed with a disease or conditions related to low butyrate levels, and an sub-optimal level of butyrate.

8. The method of claim 1, wherein said administering results in a decrease in signs or symptoms of a disease or condition.

9. The method of claim 8, wherein said disease or condition is selected from the group consisting of inflammatory bowel diseases, type II diabetes, metabolic syndrome, obesity, cancer, and graft versus host disease.

10. The method of claim 1, wherein said *Clostridium* seq 176 has a 16S rRNA V4 region sequence of SEQ ID NO:1 or sequences at least 95% identical to SEQ ID NO:1.

11. A method of treating a disease or condition associated with low levels of butyrate in the intestine of a subject, comprising:
   a) assaying a sample from a subject for the presence of *Clostridium* seq 176 and/or *Ruminococcus bromii*; and
   b) administering a composition comprising a potato starch and one or both of *Clostridium* seq 176 and/or Ruminococcus bromii to a subject lacking said *Clostridium* seq 176 and/or Ruminococcus bromii, wherein said composition comprises said *Clostridium* seq 176 and/or Ruminococcus bromii that the subject lacks.

12. The method of claim 1, further comprising administering at least one second bacteria selected from the group consisting of bacteria belonging to the taxons identified as *Faecalibacterium prausnitzii, Eubacterium rectale, Roseburia* spp., *Eubacterium hallii*, and *Anaerostipes hadrus* to said subject.

13. The method of claim 11, further comprising administering at least one second bacteria selected from the group consisting of bacteria belonging to the taxons identified as *Faecalibacterium prausnitzii, Eubacterium rectale, Roseburia* spp., *Eubacterium hallii*, and *Anaerostipes hadrus* to said subject.

14. The method of claim 13, wherein said *Roseburia* spp. is selected from the group consisting of *Roseburia* faecis, *Roseburia intestinalis*, and *Roseburia inulinivorans*.

* * * * *

SEQUENCE LISTING

```
<160> NUMBER OF SEQ ID NOS: 2

<210> SEQ ID NO 1
<211> LENGTH: 253
<212> TYPE: DNA
<213> ORGANISM: Clostridium

<400> SEQUENCE: 1
tacgtaggtg gcaagcgttg tccggattta ctgggcgtaa agggagcgta ggcggatttt      60
taagtgggat gtgaaatacc cgggctcaac ctgggtgctc cattccaaac tggaagtcta     120
gagtacagga ggggaaagcg gaattcctag tgtagcggtg aaatgcgtag agattaggaa     180
gaacaccagt ggcgaaggcg gctttctgga ctgtaactga cgctgaggct cgaaagcgtg     240
gggagcaaac agg                                                        253
```

```
<210> SEQ ID NO 2
<211> LENGTH: 253
<212> TYPE: DNA
<213> ORGANISM: Clostridium

<400> SEQUENCE: 2
tacgtaggga gcgagcgttg tccggattta ctgggtgtaa agggtgcgta ggcggccgag      60
caagtcagtt gtgaaaacta tgggcttaac ccataacgtg caattgaaac tgtccggctt     120
gagtgaagta gaggtaggcg gaattcccgg tgtagcggtg aaatgcgtag agatcgggag     180
gaacaccagt ggcgaaggcg gcctactggg ctttaactga cgctgaggca cgaaagcatg     240
ggtagcaaac agg                                                       253
```